(12) United States Patent
Ghosh et al.

(10) Patent No.: US 8,741,628 B2
(45) Date of Patent: Jun. 3, 2014

(54) **INTEGRATED PROCESS FOR THE PRODUCTION OF OIL BEARING *CHLORELLA VARIABILIS* FOR LIPID EXTRACTION UTILIZING BY-PRODUCTS OF JATROPHA METHYL ESTER (JME) PRODUCTION**

(75) Inventors: Pushpito Kumar Ghosh, Gujarat (IN); Sandhya Chandrika Prasad Mishra, Gujarat (IN); Mahesh Ramniklal Gandhi, Gujarat (IN); Sumesh Chandra Upadhyay, Gujarat (IN); Sanjiv Kumar Mishra, Gujarat (IN); Imran Pancha, Gujarat (IN); Anupama Vijaykumar Shrivastav, Gujarat (IN); Deepti Jain, Gujarat (IN); Bhumi Shethia, Gujarat (IN); Subama Maiti, Gujarat (IN); Krushnadevsinh Sukhdevsingh Zala, Gujarat (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/821,055

(22) PCT Filed: Sep. 22, 2011

(86) PCT No.: PCT/IN2011/000655
§ 371 (c)(1),
(2), (4) Date: Mar. 6, 2013

(87) PCT Pub. No.: WO2012/038978
PCT Pub. Date: Mar. 29, 2012

(65) Prior Publication Data
US 2013/0164799 A1      Jun. 27, 2013

(30) Foreign Application Priority Data
Sep. 22, 2010 (IN) .............................. 684/DEL/2010

(51) Int. Cl.
C12P 7/64        (2006.01)
(52) U.S. Cl.
CPC ..................................... C12P 7/649 (2013.01)

USPC ........ 435/257.3; 435/132; 435/166; 435/167; 435/134

(58) Field of Classification Search
None
See application file for complete search history.

(56) References Cited

U.S. PATENT DOCUMENTS 7,666,234 B2 *   2/2010   Ghosh et al. .................... 44/308
8,403,558 B2 *   3/2013   Fuchs et al. ................... 374/102

(Continued)

FOREIGN PATENT DOCUMENTS

WO    WO 2010042842 A2 *   4/2010
WO    WO 2011027353 A1 *   3/2011

OTHER PUBLICATIONS

Shihira et al., "Chlorella. Physiology and taxonomy of forty-one isolates", Maryland: University of Maryland, College Park, pp. 1-97, 1965.*

(Continued)

*Primary Examiner* — Rebecca Prouty
*Assistant Examiner* — Richard Ekstrom
(74) *Attorney, Agent, or Firm* — Ladas & Parry LLP (57) ABSTRACT

An energy efficient process for the preparation of marine microalgae *Chlorella* fatty acid methyl ester (CME) from hydrolysate of deoiled cake of *Jatropha* (JOCH) and crude glycerol co-product stream (GL7 and GL8) along with seawater diluted with tap water (1:2). A small part of the crude glycerol layer in case of JME is processed to recover glycerol for glycerol washing and the otherwise problematic still bottom is utilized for microbial synthesis of PHAs and the rest is utilized for Microalgal conversion of JME byproducts into CME. The remaining part of the methanol-depleted glycerol layer is utilized, along with hydrolysate of the *Jatropha* deoiled cake (JOCH), for single-stage Microalgal production of lipids by a marine Microalgal isolate (*Chlorella* sp.) without the need for any other nutrients. Waste streams from the microalgal processes can be discharged directly into agricultural fields as biofertilizer or recycled back in the mass cultivation.

6 Claims, 2 Drawing Sheets

(56) References Cited

U.S. PATENT DOCUMENTS

| | | | |
|---|---|---|---|
| 2008/0160591 A1* | 7/2008 | Willson et al. | 435/132 |
| 2009/0298159 A1* | 12/2009 | Wu et al. | 435/257.3 |
| 2010/0279354 A1* | 11/2010 | De Crecy | 435/71.1 |
| 2010/0330615 A1* | 12/2010 | Neto | 435/42 |
| 2011/0275118 A1* | 11/2011 | De Crecy | 435/42 |
| 2013/0005009 A1* | 1/2013 | Mody et al. | 435/161 |
| 2013/0118061 A1* | 5/2013 | Kang et al. | 44/388 |

OTHER PUBLICATIONS

Liang et al., "Fermentable sugar release from Jatropha seed cakes followiing lime pretreatment and enzymatic hydrolysis", Bioresource Technology, vol. 101, pp. 6417-6424, 2010.*

Gao et al., "Application of sweet sorghum for biodiesel production by heterotrophic microalga Chlorella protothecoides", Applied Energy, vol. 87, pp. 756-761, 2010.*

Wei et al., "Effects of cassava starch hydrolysate on cell growth and lipid accumulation of the heterotrophic microalgae Chlorella protothecoides", Journal of Industrial Microbiology and Biotechnology, vol. 36, pp. 1383-1389, 2009.*

* cited by examiner

Effect of pH on settling of the *Chlorella* sp.

INTEGRATED PROCESS FOR THE PRODUCTION OF OIL BEARING *CHLORELLA VARIABILIS* FOR LIPID EXTRACTION UTILIZING BY-PRODUCTS OF JATROPHA METHYL ESTER (JME) PRODUCTION

RELATED APPLICATION INFORMATION

This application is a 371 of International Application PCT/IN2011/000655 filed 22 Sep. 2011 entitled "Integrated Process For The Production Of Oil Bearing *Chlorella Variabilis* For Lipid Extraction Utilizing By Products Of *Jatropha* Methyl Ester (JME) Production", which was published in the English language on 29 Mar. 2012, with International Publication Number WO 2012/038978 A1, and which claims priority from Indian Patent Application 684/DEL/2010 filed 22 Sep. 2010, the content of which is incorporated herein by reference.

FIELD OF THE INVENTION

The present invention relates to integrated process for the production of oil bearing *Chlorella variabilis* for lipid extraction utilizing by-products of *Jatropha* methyl ester (JME) production from whole seeds of *Jatropha*.

The present invention further relates to an integrated process for the preparation of *chlorella* methyl ester (CME) from *Jatropha* methyl ester (JME) byproducts in a cost effective manner.

The present invention further relates to an alternative method of mixotrophic growth of microalgae (a photoautotroph) on the nutrient (C/N/P) rich waste products of JME.

BACKGROUND OF THE INVENTION

Reference may be made to Journal "Journal of Applied Phycology, 2009, 21: pp 493-507" wherein information available in the literature on Microalgal growth rates, lipid content and lipid productivities for 55 species of microalgae, including 17 Chlorophyta, 11 Bacillariophyta and five Cyanobacteria as well as other taxa is described.

Reference may be made to the Report prepared by Tom Bruton for Sustainable Energy Ireland; 2009 (www.sei.ie/algaereport), There are at least 30,000 known species of microalgae which is a very heterogeneous group and not fully explored. From the vast number of known marine and freshwater species, only handfuls are currently of commercial significance. These include *Chlorella, Spirulina* and *Haematococcus*. Of these only *Dunaliella* is predominantly a marine species. Hence, the need is to explore and exploit the Microalgae from marine ecosystem.

Reference may be made to the Journal by Ito et al. "J. Bioscience & Bioengineering, 2005, 100, pp 260-265" wherein the biochemical production of hydrogen and ethanol from the glycerol-containing wastes discharged after biodiesel manufacturing process is described. It is reported that the biochemical activity is much lower than with pure glycerol due to the presence of high salt content in the wastes.

Reference may be made to the patent WO/2008/083352 entitled "Production of biofuels using algae" describing two stage process for production of biofuels from algae including cultivation of an oil-producing algae by promoting sequential photoautotrophic and heterotrophic growth. They co-cultivate nitrogen fixing cyanobacteria to provide nitrogen as nutrient in first stage and subsequently adding sugar obtained from hydrolysis of starch and cellulose. No specific mention is made of the subject matter of the present application.

Reference may be made to the Journal by A. H. Scragg et at "Enzyme and Microbial Technology 2003, 33, pp 884-889" wherein microalgae such as the *Chlorella* spp. with a cell size in the range of 3-10 μm ideal for combustion in a diesel engine; the liquid fuel consists of an emulsion of biodiesel (transesterified rapeseed oil), a surfactant and cells of *Chlorella vulgaris* (biomass slurry) used as an unmodified stationary diesel engine for the supply of electricity is described.

Reference may be made to the review paper by Chen (Trends Biotechnology 1996, 14, 421-426) which describes algal oil production and possibility of microalgae to be cultured in heterotrophic conditions where organic carbons, such as sugars and organic acids, serve as carbon sources.

Reference may be made to the paper by Xiaoling Miao et al (Bioresource Technology 2006, 97, pp 841-846) which describes heterotrophically cultivated *Chlorella protothecoides* (using 10 g/l glucose and 0.1 g/l glycine) to accumulate as much as 55% of its dry weight as oil, compared to only 14% in cells grown photoautotrophically. This patent utilizes costly as well as edible sugars and amino acids like glucose and glycine respectively.

Reference may be made to the patent US0086937A1 by Hazelbeck et al entitled 'Photosynthetic oil production in a two-stage reactor' describing two stage reactor for growth and oil production in algae mixing nutrients which contains phosphorous, sulfur, nitrogen, carbonates, numerous trace element with dissolved $CO_2$ and constant agitation involving lot of energy inputs.

Reference may be made to the paper by Han Xu et al (Journal of Biotechnology 2006; 126, pp 499-507) which describes heterotrophic growth of *C. protothecoides* using corn powder hydrolysate having the crude lipid content of 55.2% in 3L medium in 5L biofermenters. A high density heterotrophic culture of *C. protothecoides* with CPH feeding was established in the 5 L stirred tank biofermenter. Lipid content in the algal cells cultivated in the biofermenter was 46.1%, which was a little lower than that in the Erlenmeyer flasks (55.3%). The cell growth reached maximum value (3.92 g L−1) after 144 h culture with the substrate of CPH, while the maximum value was 3.74 g L−1 with the substrate of glucose in Erlenmeyer flasks containing 300 mL medium at 28±1° C. under continuous shaking (180 rpm) and air flowing in the dark. It indicated that, it was feasible to use CPH as organic carbon to cultivate *Chlorella*.

Reference may be made to the paper by Fu-Ying Feng et al "Process Biochemistry 2005; 40; 1315-1318" wherein effects of glucose, sodium thiosulphate and a combination of these two compounds in culture medium on growth kinetics and fatty acid production of *Chlorella* sp. Has been described. Two different concentrations (2.5 mmol and 5.0 mmol) of both components in culture medium were used. They suggest that an appropriate concentration of glucose in combination with sodium thiosulphate can enhance the accumulation of lipids of *Chlorella* sp. cells.

Reference may be made to the paper by Liang, Yanna et al "Biotechnology Letters 2009; 7; 1043-1049", which describes autotrophic growth with cellular lipid content (38%), and the lipid productivity was much lower compared with those from heterotrophic growth with acetate, glucose, or glycerol. Optimal cell growth (2 g l−1) and lipid productivity (54 mg/1/day) was attained using glucose at 1% (w/v) whereas higher concentrations of glucose and glycerol were inhibitory.

Reference may be made to the paper by Chih-Hung Hsieh et al "Bioresource Technology 2009, 100(17), pp 3921-3926"

which describes *Chlorella* sp cultivated in various culture modes to assess biomass and lipid productivity. In the batch mode, the biomass concentrations and lipid content of *Chlorella* sp. cultivated in a medium containing 0.025-0.200 g $L^{-1}$ urea were 0.464-2.027 g $L^{-1}$ and 0.661-0.326 g $g^{-1}$, respectively. The maximum lipid productivity of 0.124 g $L^{-1}$ occurred in a medium containing 0.100 g $L^{-1}$ urea. In the fed-batch cultivation, the highest lipid content was obtained by feeding 0.025 g $L^{-1}$ of urea during the stationary phase, but the lipid productivity was not significantly increased. However, a semi-continuous process was carried out by harvesting the culture and renewing urea at 0.025 g $L^{-1}$ each time when the cultivation achieved the early stationary phase. The maximum lipid productivity of 0.139 g $d^{-1}$ $L^{-1}$ in the semi-continuous culture was highest in comparison with those in the batch and fed-batch cultivations. Reference may be made to the paper by Mandal et al (Applied Microbiology Biotechnology 2009, 84: 281-291) which describes microalgae such as *Scenedesmus obliquus* accumulating lipid inside the cell under nitrogen and phosphorous deficient condition. The lipid content increase significantly up to 43% of dry cell weight under N-deficiency.

Reference may be made to the paper by Demirbas "Energy Sources, Part A, 31:163-168, 2009", which describes comparative lipid profiling of *Chlorella protothecoides* and *Cladophora fracta* which contains 29.4% cell dry weight and 14.2% cell dry weight respectively.

Reference may be made to the paper by Cheng et al "Journal of chemical technology & Biotechnology 2009; 84,5; pp 777-781" which describes *Chlorella protothecoides* utilizing hydrolysate of Jerusalem artichoke tuber (*Helianthus tuberosus* L) as carbon source and accumulated lipid in vivo, with lipid content as high as 44% cdw, and a carbon source to lipid conversion ratio of about 25% in a 4-day scale cultivation. The lipids were extracted and then converted into biodiesel by transesterification. Cetane acid methyl ester, linoleic acid methyl ester and oleic acid methyl ester were the dominating components of the biodiesel produced. Unsaturated fatty acids methyl ester constituted over 82% of the total biodiesel content.

Reference may be made to the paper by Bertoldi et al "Grasas Y Aceites 2006; 57 (3) pp 270-274" wherein Lipids, fatty acids composition and carotenoids of *Chlorella vulgaris* cultivated in industrial and agriculture waste waters, the results "showed that lipid contents did not present" significant difference .The use of hydroponic wastewater as an alternative culture medium for the cultivation of *Chlorella vulgaris* generates good perspectives for lipid, fatty acid and carotenoid production.

Reference may be made to the paper by Xiufeng Li et al "Biotechnology and Bioengineering 2007, 98(4) pp 764-771", which describes heterotrophic *Chlorella protothecoides* focused on scaling up fermentation in bioreactors. through substrate feeding and fermentation process controls, the cell density of *C. protothecoides* achieved 15.5 $gL^{-1}$ in 5 L, 12.8 $gL^{-1}$ in 750 L, and 14.2 $gL^{-1}$ in 11,000 L bioreactors, respectively. Resulted from heterotrophic metabolism, the lipid content reached 46.1%, 48.7%, and 44.3% of cell dry weight in samples from 5 L, 750 L, and 11,000 L bioreactors, respectively.

Reference may be made to the paper by Wei et al "Journal of Industrial Microbiology Biotechnology DOI 10.1007/s10295-009-0624-x", which describes heterotrophic growth of *Chlorella protothecoides* using cassava starch hydrolysate i.e. CSH made by two step enzymatic process evolving amylase and gluco-amylase as the organic carbon source, the highest biomass and the maximum total lipid yield obtained were 15.8 and 4.19 g/L, representing increases of 42.3 and 27.7%, respectively, compared to using glucose as the organic carbon source.

It will be evident from the prior art that no cost-effective process has been disclosed for production of Microalgal biomass from biodiesel co-product streams and even with the use of costly co-nutrients and cumbersome 2-step process. The present invention seeks to overcome all the basic limitations and to evolve a novel, simplified and cost-effective process of producing lipids from the microalgal biomass generated from glycerol co-product stream of methyl ester process starting from *Jatropha* whole seed capsule. Several associated improvements in the process e.g. best utilization of problematic waste, particularly oil sludge generated during mechanical expelling of oil and still bottom of glycerol distillation process, also form part of the present invention, besides involving fed batch process for initially increasing the biomass productivity and then improving the lipid content i.e. lipid IC productivity.

OBJECTIVE OF THE INVENTION

Main objective of the present invention is to provide integrated process for the production of oil bearing *Chlorella variabilis* for lipid extraction utilizing by-products of *Jatropha* methyl ester (JME) production from whole seeds.

Another objective of the present invention is to provide an integrated process for the cost effective preparation of nutrient media for the Mixotrophic growth of *Chlorella variabilis* from *Jatropha* methyl ester (JME) by-products obtained from the whole dried fruits of *Jatropha*.

Another objective of the present invention is to provide an integrated process for the enhancement of lipid productivity through Mixotrophic growth of the microalgae (*Chlorella* sp.) in *Jatropha* methyl ester byproducts for making fatty acid methyl ester.

Another objective of the present invention is to produce Microalgal biodiesel with least energy inputs and almost zero effluent discharge.

Still another object of the present invention is to utilize the crude glycerol after mopping up of methanol as a carbon and nutrient source in growth and production media for microalgal growth and production of oil/lipid in cost-effective manner.

Another object of the present invention is to protect the *Chlorella variabilis* by adding a UV-specific dye (UV-absorbent) during outdoor mass culture from UV-damages especially in summer of India (40° C.-50° C.) maintaining the viability of the culture.

Another object of the present invention is to utilize the cake obtained after expelling oil from *Jatropha* seeds as a source of amino acids and other nutrients in the growth medium and thereby to dispense with complex media such as Zarrouk's medium, M4N medium, ASNIII medium and another sugar containing growth medium.

Another object of the present invention is to show that toxic impurities such as phorbol esters and curcin which are indicated to be present in the oil cake do not hamper oil production in the processes of the present invention.

Another object of the present invention is to demonstrate production of lipids with desired quality of fatty acids.

Another object of the present invention is to show that a marine *Chlorella variabilis* isolate from the Indian coast gives a yield of 20-35% with respect to cell dry weight by inoculating the culture directly into a medium containing the alkaline crude glycerol layer and the hydrolysate derived from deoiled *Jatropha* cake and without use of any other nutrient/micronutrients and without any other intervention such as sparging, pH adjustment, temperature control, agitation, aeration, etc.

Another object of the present invention is to achieve such lipid production in the simplest and cheapest manner and in the shortest possible time.

SUMMARY OF THE INVENTION

Accordingly, present invention provides an integrated process for the production of oil bearing *Chlorella variabilis* for lipid extraction utilizing by-products of *Jatropha* methyl ester (JME) production from whole dried fruits of *Jatropha* and the said process comprising the steps of:
  i. providing deoiled cake having 4-6% (w/w) nitrogen of *Jatropha* seeds by known method;
  ii. hydrolysating the deoiled cake as provided in step (i) with hot acidic aqueous solution followed by adjusting pH in the range of 5.5 to 8.5 with alkaline materials to obtain a nitrogen-rich *Jatropha* oil cake hydrolysate (JOCH);
  iii. providing 1-5% (w/v) of the crude glycerol containing methanol-depleted glycerol layer (GL7 and GL8) as a growth-cum production medium for marine *Chlorella variabilis* by known method;
  iv. inoculating 1-10% (v/v) of the marine *Chlorella variabilis* seed culture into growth-cum-production medium as provided in step (iii) and 1-10% (v/v) of *Jatropha* oil cake hydrolysate as prepared in step (ii) and incubating for a period in the range of 7 to 15 days at a pH in the range of 7.0-8.0 at a temperature in the range of 25-40° C. to obtain lipid containing biomass;
  v. optionally inoculating 1-10% (v/v) of the marine *Chlorella variabilis* seed culture on the $1^{st}$ day of seed culture inoculation with tap water, for initial 4 to 10 days incubation with only seawater or 1:2 diluted seawater in tap water and after $4^{th}$ to $10^{th}$ day subsequently adding GL7 to obtain lipid containing biomass;
  vi. optionally inoculating 1-10% (v/v) of the marine *Chlorella variabilis* seed culture on the $1^{st}$ day of seed culture inoculation with tap water, for initial 4 to 10 days incubation with only seawater or 1:2 diluted seawater in tap water and after $4^{th}$ to $10^{th}$ day subsequently adding GL8 to obtain lipid containing biomass;
  vii. drying the biomass as obtained in step (iv to vi) in sun or directly using the wet biomass for lipid extraction;
  viii. extracting the lipid from biomass as obtained in step (vii) by known method.

In an embodiment of the present invention, acid used is selected from $H_3PO_4/H_2SO_4$.

In yet another embodiment of the present invention, alkaline material is selected from crude glycerol layer, potassium hydroxide and magnesium hydroxide.

In yet another embodiment of the present invention, 2,5-thiophenediylbis(5-tert-butyl-1,3-benzoxazole) UV-specific dye is added during outdoor mass to protect from UV damage especially in summer of India (40° C. to 50° C.) maintaining the viability of the culture.

In yet another embodiment of the present invention, methanol-depleted glycerol layer is obtained by mopped up of the ethanol from the glycerol layer by known method.

In yet another embodiment of the present invention, yield of the lipid with respect to cell dry weight were in the range of 20 to 35%.

DETAILED DESCRIPTION OF THE INVENTION

Figure 1:
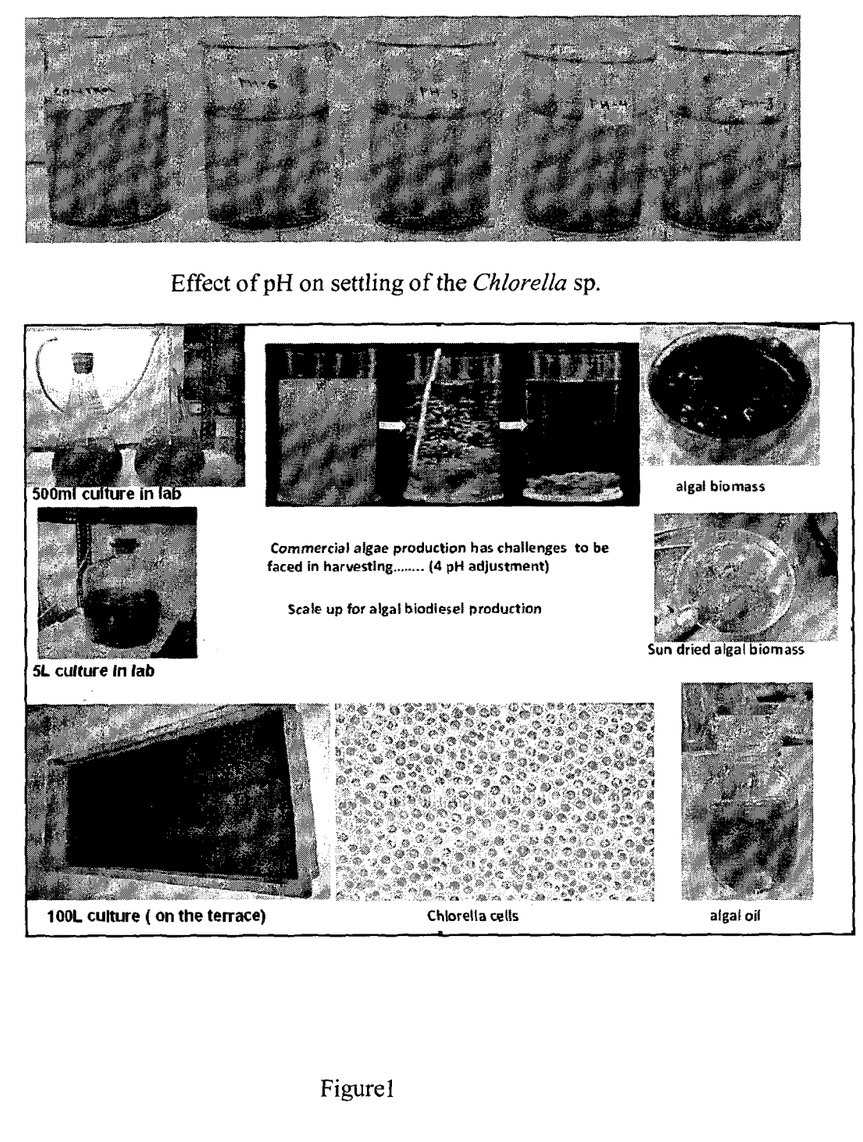
FIG. 1 represent effect of pH on settling of the *Chlorella variabilis* and scale up processing of *Chlorella*. The integrated scheme of the present invention is also shown in FIG. 1.
Figure 2:
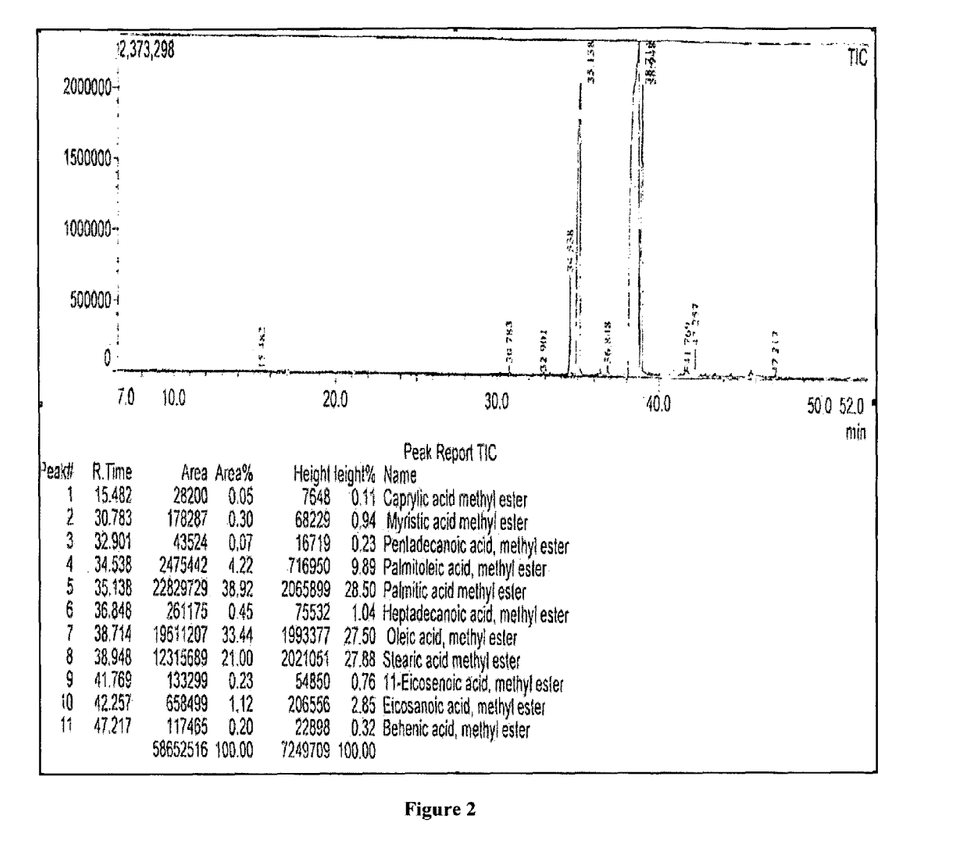
FIG. 2 shows GCMS of *chlorella* fatty acid methyl ester.

The biochemical process of photosynthesis provides algae with the ability to convert solar energy into chemical energy through chlorophyll as antenna for trapping the radiation required for building its food. During cell growth, this chemical energy is used to drive synthetic reaction, such as the formation of sugars or the fixation of nitrogen into amino acids for protein synthesis. Excess chemical energy is stored in the form of fats and oils as triglycerides. Therefore, it can be seen that cell growth and triglycerides production compete for the same chemical energy. As a result, the simultaneous rates of growth and oil production are inversely related.

Present invention provides an integrated process for the cost effective preparation of nutrient media for the Mixotrophic growth of *Chlorella variabilis* from *Jatropha* methyl ester (biodiesel) by-products obtained from the whole dried fruits of *Jatropha* and the said process comprising the following steps:
  a. mechanically deshelling the sun-dried fruits and collecting separately the shells and the seeds;
  b. mechanically expelling the oil from the seeds by known technique; Deoiled cake is obtained in the prior art [(Ghosh et al US pre-grant publication No is 2006/0080891 A1) (1838/DEL/2009 dated 7 Sep. 2009)];
  c. utilizing the small amounts of waste oil generated in (b) above as a binder for briquetting of the seed shells;
  d. treating a part of the deoiled cake obtained in (b) above with acid to hydrolyse the cake and to obtain a nitrogen-rich hydrolysate;
  e. utilising the larger part of the methanol-depleted glycerol layer as a lipid production medium for marine *Chlorella variabilis* and the remaining residues for the production of biodegradable polymer i.e. polyhydroxyalkanoates (PHAs) through marine bacteria MTCC 5345 (as in patent filed 1838/DEL/2009 dated 7 Sep. 2009);
  f. inoculating 1-10% (v/v) of the marine *Chlorella variabilis* seed culture into growth-cum-production medium containing 1-5% (w/v) of the crude glycerol of step (1) and 1-10% (v/v) of *Jatropha* oil cake hydrolysate as prepared in step (d) and incubating for a period in the range of (7-15 days) at a pH of 7.0-8.0 at a temperature in the range of 25-40° C.;
  g. inoculating 1-10% (v/v) of the marine *Chlorella* sp. in *Jatropha* oil cake hydrolysate as above on the $1^{st}$ day of seed culture inoculation with tap water, only seawater and 1:2 diluted seawater in tap water for initial (4-10days) incubation and subsequently adding GL7 after $4^{th}$ to $10^{th}$ day for lipid production.
  h. inoculating 1-10% (v/v) of the marine *Chlorella* sp. in *Jatropha* oil cake hydrolysate as above on the $1^{st}$ day of seed culture inoculation with tap water, only seawater and 1:2 diluted seawater in tap water for initial (4-10 days) incubation and subsequently adding GL8 after $4^{th}$ to $10^{th}$ day for lipid production.
  i. drying the biomass in sun or directly using the wet biomass for lipid extraction and making biodiesel.

The hydrolysate obtained in step (d) was extracted by treating *Jatropha* oil cake having 4-6% (w/w) nitrogen, with hot acidic aqueous solution of $H_3PO_4/H_2SO_4$ and thereafter adjusting pH to 5.5-8.5 with alkaline materials such as crude glycerol layer, potassium hydroxide and magnesium hydroxide to yield salts which have buffering action and contributing to the nutrient value of the hydrolysate instead of as problematic electrolytes which retard the bioconversion process of the prior art.

The methanol has been mopped up from the glycerol layer in the process as described in the Ghosh et al US-patent entitled "An improved process for the preparation of fatty acid methyl ester (Biodiesel) from triglycerides oil through transesterification" pre-grant publication No is 2006/0080891 A1 dated 20 Apr. 2006; and the residues left after a successful cycle, consisting mainly of solids and free liquids that have no value in terms of further distillable solvent/product are considered as a good source of nutrients. production by Microalgal conversion processes of steps (d to i) were carried out with a marine *Chlorella variabilis* isolate and the lipid yields with respect to cell dry weight were in the range of (20 to 35%).

The above steps may equally apply to a variety of Microalgal spp.

The microalgae was grown in Zarrouk's medium and thereafter, it was inoculated into the production medium containing 1-5% of glycerol still bottom and other essential nutrients and the contents left to incubate under static ambient condition for 7-15 days.

The microalgae was grown in seawater, tap water, seawater and tap water in 1:2 ratio, 1-5% (w/v) of GL8 and other essential nutrients and the contents left to incubate under static and agitated condition (100-300 rpm) for 7-15 days.

The microalgae was grown in only seawater, only tap water, and combination of sea water:tap water 1:2, 1-5% (w/v) of glycerol still bottom (GL7 and GL8 separately) and other essential nutrients and the contents left to incubate under static ambient condition for 7-15 days.

The microalgae were grown in seawater, Tap water and seawater:tap water 1:2, 1-10% (w/v) JOCH with other micronutrients for 7-15 days under static condition.

The microalgae were grown in seawater, tap water, and seawater:tap water 1:2, 1-5% (w/v) GL7 with other micronutrients for 7-15 days under static condition.

The microalgae were grown in seawater, tap water and seawater:tap water 1:2, 1-5% (w/v) GL8 with other micronutrients for 7-15 days under static condition.

The microalgae was grown in seawater, tap water, and seawater:tap water 1:2 with mixture of *Jatropha* deoiled cake hydrolysate (JOCH) 1-10% and glycerol still bottom 1-5% w/v in seawater, tap water and 1:2 ratio mixer of sea water and tap water with other essential nutrients and the contents left to incubate under static ambient condition for 7-15 days.

The microalgae were grown in sea water, tap water and sea water:tap water 1:2 initially with 1-10% (v/v) of *Jatropha* oil cake Hydrolysate (JOCH) subsequently adding GL7 after $4^{th}$ and 10th day under static condition for 15 days.

The lipid was extracted by known method. (ref Bligh, E. G. and Dyer, W. J. 1959. A rapid method for total lipid extraction and purification. *Can. J. Biochem. Physiol.* 37:911-917.) The fatty acid profile shows the applicability of the lipid in making biodiesel.

The aim of the present invention is to develop an integrated process for the production of Microalgal biomass utilizing *Jatropha* methyl ester co-products. With regards to the deoiled *Jatropha* cake and crude glycerol layer, the question arises as to what is the highest level of simplification possible in its effective use. As disclosed in the present invention, if the excess methanol in the glycerol layer can be removed by simple means, then the rest of the mass can be utilized directly for preparation of lipids in microalgae by simple and cost effective means. Once the methanol is mopped up as in the prior art (Ghosh et al, US pre-grant publication No is 2006/0080891 A1) (1838/DEL/2009 dated 7 Sep. 2009) the glycerol layer is demonstrated to be an excellent source of nutrient for efficient and cost-effective production of lipids by a marine *Chlorella* culture isolated in the course of the invention. The hydrolysate produced from *Jatropha* deoiled cake obtained through reactive extraction with hot phosphoric acid/sulphuric acid is shown to be an ideal complementary partner to the crude glycerol, the two in tandem providing the nutrients required for the lipid production by the marine *Chlorella* culture under ambient conditions. The two together also help to neutralize (acid-base) each other to some extent thereby driving down the cost of neutralization. There are several additional inventions such as merging the normal 2-stages operation process into a single step, dispensing altogether with all nutrients/micronutrients by deriving the essential phosphate buffers and essential elements from the hydrolysate and glycerol layer besides carbon and nitrogen. In a decentralized operation, where such a plant will be set up in the vicinity of agricultural fields, the supernatant after recovery of harvestable biomass can be discharged directly into the field for soil fertigation or can even be used as a foliar spray, besides recycling in the Microalgal mass cultivation (outdoors).

It is further demonstrated that the still bottom remaining after glycerol recovery is an equally effective nutrient and promoter for the lipid production by a marine Microalgal culture, the efficiency of production being nearly twofold higher than with pure glycerol. Thus, the problematic waste is found to be an ideal source of nutrients.

All of these inventions taken together lead to an improved integrated process of production of methyl ester from sun dried whole seed capsules of *Jatropha curcas* with gainful utilization of co-product streams.

The strain used in this invention was isolated from west coast of India (located between N 20° 41.341' latitude and E 70° 53.734' longitude).

The deposit of the biological material used in the invention that is *CHLORELLA VARIABILIS* has been made at ATCC, USA in accordance with the provisions of the Budapest treaty.

However, till date the applicants were unable to obtain the deposit number in respect thereof. The deposit number of the strain will be furnished as soon as we obtain it from the ATCC, USA.

The *Chlorella* species used for the purposes of the present invention bears. 98% similarity with the already reported *Chlorella* strains. It was observed that the strain *Chlorella variabilis* used in the present invention can be interchangeably used with the *Chlorella variabilis* strain already available at ATCC vide No. 50258 (NC64A).

Inventive Features of the Invention
  (i) Isolating robust marine microalgae which enables lipid to be produced from the still bottom in a mixotrophic manner that is more advantageous than under photoautotrophic growth of the microalgae thereby converting a problematic waste into lipid which is a useful raw material for making fatty acid methyl ester (biodiesel).
  (ii) Identifying through the process of screening of microalgae a potent isolate which efficiently utilizes the larger volume of crude glycerol layer directly, together with the hydrolysate of *Jatropha* deoiled cake, as the only nutrients in the process leading to production of lipid (20-40%) with respect to cell dry weight. Further, combining the steps of growth and production undertaken separately in the conventional processes of lipid production into a single operation and thereby simplifying the process. Also dispensing with the need for temperature control after demonstrating tolerance of the process to temperature variations over 30-45° C.

(iii) recognizing that in preparing the hydrolysate of deoiled cake used in the microalgal process, it is advantageous to use phosphoric acid and thereafter to neutralize the acid extract with the alkaline glycerol layer itself—and additional KOH/Mg(OH)$_2$ as may be required—so that the resultant salts support the lipid productivity instead of thwarting it.

(iv) The microalgae could be grown in sea water, tap water and sea water:tap water 1:2 initially with 1-10% (v/v) of *Jatropha* oil cake Hydrolysate (JOCH) subsequently adding GL7 after 4$^{th}$ and 10th day under static condition for 15 days.

(v) Utilizing the small amount of residual biomass of microalgae, which is inevitably generated during the process of mechanical expelling and causes problems of disposal in either aqua feed/poultry feed/cattle feed—, or to produce denser and stronger briquettes from the empty shells as in the prior art (Ghosh et al, US pre-grant publication No is 2006/ 0080891 A1) (1838/DEL/2009 dated 7 Sep. 2009).

Lipids from *Jatropha* Biodiesel Waste Residues Through Microalgae

| Table Inductively coupled Plasma (ICP) results showing Elemental analysis of GL7 and GL8 | | |
|---|---|---|
| Analyte (mg/L) | GL7 | GL8 |
| Calcium | 3.263 | 8.189 |
| Cadmium | 0.002 | 0.002 |
| Cobalt | 0.000 | 0.002 |
| Chromium | 0.005 | 0.023 |
| Copper | 0.075 | 0.046 |
| Iron | 0.360 | 0.554 |
| Potassium | 48.90 | 21.63 |
| Magnesium | 2.183 | 3.552 |
| Manganese | 0.022 | 0.040 |
| Molybdenum | 0.004 | 0.004 |
| Sodium | 17.21 | 38.24 |
| Nickel | 0.006 | 0.022 |
| Lead | 0.015 | 0.152 |
| Zinc | 0.814 | 0.131 |

| | Biodesel waste residue (BWR3) | | | | | | | | |
|---|---|---|---|---|---|---|---|---|---|
| | Base medium | BWR3 | BWR6 | JOCH | Light | A/S | Biomass (gram) | lipid (gram) | content of lipid (%) |
| Example 1 | 200 ml ZM | | | | L | S | 0.801 | 0.13 | 16.22 |
| Example 2 | 200 ml SW | | | | L | S | 0.347 | 0.0506 | 14.58 |
| Example 3 | 200 ml SW | | | | D | S | 0.217 | 0.0312 | 14.37 |
| Example 4 | 200 ml SW | 1% | | | L | A | 0.367 | 0.054 | 14.71 |
| Example 5 | 200 ml SW | 2% | | | L | A | 0.42 | 0.077 | 18.33 |
| Example 6 | 200 ml (SW:TW: 1:2) | 1% | | | L | A | 0.387 | 0.087 | 22.48 |
| Example 7 | 200 ml (SW:TW: 1:2) | 2% | | | L | A | 0.453 | 0.097 | 21.41 |
| Example 8 | 200 ml SW | 1% | | | L | S | 0.447 | 0.085 | 19.01 |
| Example 9 | 200 ml SW | 2% | | | L | S | 0.407 | 0.074 | 18.18 |
| Example 10 | 200 ml (SW:TW: 1:2) | 1% | | | L | S | 0.463 | 0.125 | 26.99 |
| Example 11 | 200 ml (SW:TW: 1:2) | 2% | | | L | S | 0.487 | 0.163 | 33.47 |
| Example 12 | 200 ml (SW:TW: 1:2) | 1% | | | D | S | 0.398 | 0.0863 | 21.68 |
| Example 13 | 200 ml (SW:TW: 1:2) | 2% | | | D | S | 0.378 | 0.0839 | 22.19 |
| Example 15a | 1000 ml TW | | | 1% | L | S | 3.34 | 0.18 | 5.38 |
| Example 15b | 1000 ml TW | | | 2% | L | S | 1.9 | 0.1 | 5.26 |
| Example 15 c | 1000 ml TW | | | 5% | L | S | 1.75 | 0.09 | 5.14 |
| Example 15 d | 1000 ml TW | | | 10% | L | S | 0.67 | 0.15 | 22.38 |
| Example 16a | 1000 ml TW | | 1% | | L | S | 2.36 | 0.24 | 10.16 |

-continued

Biodesel waste residue (BWR3)

| | Base medium | BWR3 | BWR6 | JOCH | Light | A/S | Biomass (gram) | lipid (gram) | content of lipid (%) |
|---|---|---|---|---|---|---|---|---|---|
| Example 16b | 1000 ml TW | | 2% | | L | S | 7.15 | 0.04 | 0.55 |
| Example 16c | 1000 ml TW | | 5% | | L | S | 6.84 | 0.03 | 0.43 |
| Example 17a | 1000 ml TW | | 2% | 2% | L | S | 2.8 | 0.2 | 7.14 |
| Example 17b | 1000 ml TW | | 2% | 5% | L | S | 1.75 | 0.34 | 19.42 |
| Example 17c | 1000 ml TW | | 2% | 10% | L | S | 3.1 | 0.7 | 22.58 |
| Example 18a | 200 ml SW | | 1% (After 10 Days) | 1% | L | S | 0.62 | 0.132 | 21.29 |
| Example 18b | 200 ml (SW:TW: 1:2) | | 1% (after 10 days) | 1% | L | S | 0.47 | 0.103 | 21.91 |
| Example 18C | 200 ml SW | | 1% | 1% | L | S | 0.51 | 0.101 | 19.80 |
| Example 18d | 200 ml (SW:TW: 1:2) | | 1% | 1% | L | S | 0.25 | 0.0401 | 16.04 |
| Example 21a | 200 ml SW | | 2% BWR-6 (after 10 days) | 1% | L | S | 0.441 | 0.0455 | 10.31 |
| Example 21b | 200 ml (SW:TW: 1:2) | | 2% BWR-6 (after 10 days) | 1% | L | S | 0.437 | 0.048 | 10.98 |
| Example 21c | 200 ml SW | | 5% BWR-6 (after 10 days) | 1% | L | S | 0.558 | 0.0785 | 14.06 |
| Example 21d | 200 ml (SW:TW: 1:2) | | 5% BWR-6 (after 10 days) | 1% | L | S | 0.454 | 0.1505 | 33.14 |
| Example 22a | 200 ml SW | | 2% BWR-6 (After 4 Days) | 1% | L | S | 0.344 | 0.014 | 4.06 |
| Example 22 b | 200 ml (SW:TW: 1:2) | | 2% BWR-6 (After 4 Days) | 1% | L | S | 0.302 | 0.019 | 6.29 |
| Example 22c | 200 ml SW | | 5% BWR-6 (After 4 Days) | 1% | L | S | 0.3785 | 0.0524 | 13.84 |
| example 22d | 200 ml (SW:TW: 1:2) | | 5% BWR-6 (After 4 Days) | 1% | L | S | 0.2635 | 0.0217 | 8.23 |
| Example 23 | 100 L Zarrouk's medium (1:2 in tap water) | | | | L | S | 401.21 | 97.29 | 24.24 |
| Example 24 | 100 L TW | 2% | | | L | S | 380.12 | 90.53 | 23.81 |
| Example 25 | 100 L(Sw:TW: 1:2 | 2% | | | L | S | 440.01 | 150.61 | 34.22 |

EXAMPLES

The following examples are given by way of illustration and therefore should not be construed to limit the scope of the present invention.

Example 1

*Chlorella* sp was found to be one of the most efficient algae and has been used in the present invention. 200 ml of Zarrouk's medium was prepared comprising 16.8 gram Sodium bicarbonate, 0.5 g di-Potassium hydrogen phosphate, 2.5 gram Sodium nitrate, 0.2 g Magnesium sulphate, 1.0 gram Sodium chloride, 0.01 gram Ferrous sulphate, 1.0 g potassium sulphate, 0.04 gram Calcium Chloride and 0.08 g EDTA dissolved in one liter of distilled water. The medium was then autoclaved at 121° C. for 20 minutes. The medium is inoculated With 20% of *Chlorella* culture (OD 1.4-1.6 at 540 nm) Flask was kept in static condition at 30° C. Optical density of culture was monitored at regular interval of 3 days. After 21 days, the cells were harvested by centrifuging and the pellet obtained was oven dried at 60° C. to get cell dry weight of 0.801 g having lipid content of 0.13 g and 16.22% cell dry weight.

Example 2

*Chlorella variabilis* was grown in 200 ml of sea water in static condition under light incubation. Growth rate was measured spectrophotometrically (OD at 540 nm) up to 16 days. After 16 days; the cell mass was harvested by centrifugation at 11,000 rpm for 10 min at 30° C. and cell pellet was washed twice with distilled water and dried in oven (60° C.) for 16 hr. Lipid was extracted from dried biomass using Chloroform: Methanol (2:1), and after evaporation of solvent the total lipid was obtained. Biomass obtained was 0.347 g having lipid content of 0.0506 gram, and 14.58% cell dry weight.

Example 3

*Chlorella variabilis* was grown in sea water in static condition under dark. Growth rate was measured spectrophotometrically (OD at 540 nm) up to 16 days. After 16 days; the cell mass was harvested by centrifugation at 11,000 rpm for 10 min at 28° C. and cell pellet was washed twice with distilled water and dried in oven at 60° C. for 16 h. Lipid was extracted from dried biomass using Chloroform:Methanol (2:1), and after evaporation of solvent the total Lipid was obtained. Biomass obtained was 0.217 g having lipid content of 0.0312 g, and 14.37% cell dry weight.

Example 4

*Chlorella variabilis* was grown in sea water with 1% of *Jatropha* biodiesel waste residues (GL8/BWR3) in agitated condition incubated under light intensity of 60 µE m$^{-2}$s$^{-1}$ provided by cool-white fluorescent tubes with a dark:light cycle of 12:12 h. Growth rate was measured spectrophotometrically (OD at 540 nm) up to 16 days. After 16 days; the cell mass was harvested by centrifugation at 11,000 rpm for 10 min at 30° C., and cell pellet was washed twice by distilled water and dried in oven at 60° C. for 16 h. Lipid was extracted from dried mass using Chloroform:Methanol (2:1), and after evaporation of solvent the total lipid was obtained. From the dried biomass 0.367 g of *Chlorella* sp., 0.054 g of lipid content i.e. 14.71% cell dry weight.

Example 5

*Chlorella variabilis* was grown in sea water with 2% of *Jatropha* biodiesel waste residues (GL8/BWR3) in agitated condition incubated under light intensity of 60 µE m$^{-2}$s$^{-1}$ provided by cool-white fluorescent tubes with a dark:light cycle of 12:12 h. Growth rate was measured spectrophotometrically (OD at 540 nm) up to 16 days. After 16 days; the cell mass was harvested by centrifugation at 11,000 rpm for 10 min at 27° C. and cell pellet was washed twice by distilled water and dried in oven at 60° C. for 16 h. Lipid was extracted from dried mass using Chloroform:Methanol (2:1), and after evaporation of solvent the total lipid was obtained. From the dried biomass 0.420 g of *Chlorella* sp., 0.077 g of lipid content i.e. 18.33% cell dry weight.

Example 6

*Chlorella variabilis* was grown in diluted sea water (1:2 in tap water) with 1% of *Jatropha* biodiesel waste residues (GL8/BWR3) in agitated condition under light incubation. Growth rate was measured spectrophotometrically (OD at 540 nm) up to 16 days. After 16 days; the cell mass was harvested by centrifugation at 11,000 rpm for 10 min at 26° C. and cell pellet was washed twice with distilled water and dried in oven at 60° C. for 16 hr. Lipid was extracted from dried biomass using Chloroform:Methanol (2:1); and after evaporation of solvent the total lipid was obtained. Biomass obtained was 0.387 g having lipid content of 0.087 mg, and 22.48% cell dry weight.

Example 7

*Chlorella variabilis* was grown in diluted sea water (1:2 in tap water) with 2% of *Jatropha* biodiesel waste residues (GL8/BWR3) in agitated condition under light incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. for 16 hr. Lipid was extracted from dried biomass using Chloroform:Methanol (2:1), and after evaporation of solvent the total Lipid was obtained. Biomass obtained was 0.453 g having lipid content of 0.097 g, and 21.41% cell dry weight.

Example 8

*Chlorella variabilis* was grown in sea water with 1% of *Jatropha* biodiesel waste residues (GL8/BWR3) in static condition under light incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. for 16 hr. Lipid was extracted from dried biomass using Chloroform: Methanol (2:1), and after evaporation of solvent the total lipid was obtained. Biomass obtained was 0.447 g having lipid content of 0.085 g, and 19.01% cell dry weight.

Example 9

*Chlorella variabilis* was grown in sea water with 2% of *Jatropha* biodiesel waste residues (GL8/BWR3) in static condition under light incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. for 16 hr. Lipid was extracted from dried biomass using Chloroform: Methanol (2:1), and after evaporation of solvent the total lipid was obtained. Biomass obtained was 0.407 g having lipid content of 0.074 g, and 18.18% cell dry weight.

Example 10

*Chlorella variabilis* was grown in diluted sea water (1:2 in tap water) with 1% of *Jatropha* biodiesel waste residues (GL8/BWR3) in static condition under light incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. for 16 hr. Lipid was extracted from dried biomass using Chloroform:Methanol (2:1), and after evaporation of solvent the total lipid was obtained. Biomass obtained was 0.463 g having lipid content of 0.125 g, and 26.99% cell dry weight.

Example 11

*Chlorella variabilis* was grown in diluted sea water (1:2 in tap water) with 2% of *Jatropha* biodiesel waste residues (GL8/BWR3) in static condition under light incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. for 16 hr. Lipid was extracted from dried biomass using Chloroform:Methanol (2:1), and after evaporation of solvent the total lipid was obtained. Biomass obtained was 0.487 g having lipid content of 0.163 g, and 33.47% cell dry weight.

Example 12

*Chlorella variabilis* was grown in diluted sea water (1:2 in tap water) with 1% of *Jatropha* biodiesel waste residues (GL8/BWR3) in static condition under dark incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. for 16 hr. Lipid was extracted from dried biomass using Chloroform:Methanol (2:1), and after evaporation of solvent the total lipid was obtained. Biomass obtained was 0.398 g having lipid content of 0.0863 g, and 21.68% cell dry weight.

Example 13

*Chlorella variabilis* was grown in diluted sea water (1:2 in tap water) with 2% of *Jatropha* biodiesel waste residues (GL8/BWR3) in static condition under dark incubation. Growth rate was measured spectrophotometrically (OD at 540 nm) up to 16 days. After 16 days; the cell mass was harvested by centrifugation at 11,000 rpm for 10 min at 30° C., and cell pellet was washed twice with distilled water and dried in oven at 60° C. over night. Lipid was extracted from dried biomass using Chloroform:Methanol (2:1), and after evaporation of solvent the total lipid was obtained. Biomass obtained was 0.378 mg having lipid content of 0.0839 g, and 22.19% cell dry weight.

Example 14

The spent glycerol layer, GL 7, was utilized as nutrient source for Microalgal production of lipid. GL7 was utilized directly for accumulation of lipid in Microalgae *Chlorella*. *Jatropha* oil cake hydrolysate (JOCH) was extracted by treating *Jatropha* oil cake, having 4-6% (w/w) N, with hot acidic aqueous solution of $H_3PO_4/H_2SO_4$ and thereafter adjusting pH suitably with alkaline materials such as crude glycerol layer, potassium hydroxide and magnesium hydroxide to yield salts which have buffering action and also contribute to the nutrient value of the hydrolysate. Isolated microalgae *Chlorella variabilis* was used for accumulation of lipid inside the cell using the GL-7 and JOCH for growth and production.

Example 15

*Chlorella variabilis* was grown with 1% JOCH, 2% JOCH, 5% JOCH and 10% JOCH, with tap water to grow up the cells of *Chlorella variabilis* under static condition with light. Growth rate was measured spectrophotometrically (OD at 540 nm) up to 21 days. After 21 days; the cell mass was harvested by centrifugation at 11,000 rpm for 10 min at 30° C., and cell pellet was washed two times by distilled water and dried in oven (60° C.) for 16 hr. Lipid was extracted from weighed dried mass using Chloroform:Methanol (2:1), and after evaporation of solvent the total lipid was obtained. In the 1% JOCH highest biomass was obtained but % of lipid content is less.

This example teaches us that, for biomass production 1% of JOCH is useful, which can be used for biomass production but not lipid. For lipid accumulation after enhancement of biomass, lipid accumulation can be achieved.

TABLE 1

| Day | 1% JOCH Example 15a | 2% JOCH Example 15b | 5% JOCH Example 15c | 10% JOCH Example 15d |
|---|---|---|---|---|
| Dry biomass (gram) | 3.34 | 1.9 | 1.75 | 0.67 |
| Lipid (gram) | 0.18 | 0.1 | 0.09 | 0.15 |
| Yield % | 5.38 | 5.26 | 5.14 | 22.38 |

Example 16

*Chlorella variabilis* was grown with 1% GL7, 2% GL7, 5% GL7 with tap water to grow the cells of *Chlorella variabilis* in static condition with light. Growth rate was measured spectrophotometrically (OD at 540 nm) up to 21 days. After 21 days; the cell mass was harvested by centrifugation at 11,000 rpm for 10 min at 30° C., and cell pellet was washed twice by distilled water and dried in oven (60° C.) for 16 hr. Lipid was extracted from dried biomass using Chloroform:Methanol (2:1), and after evaporation of solvent the total lipid was obtained. In the 2% GL7 highest biomass was obtained but % of lipid content is less.

TABLE 2

| Day | 1% GL-7 Example 16a | 2% GL-7 Example 16b | 5% GL-7 Example 16c |
|---|---|---|---|
| Dry biomass (gram) | 2.36 | 7.15 | 6.84 |
| Lipid (gram) | 0.24 | 0.04 | 0.03 |
| Yield % | 10.16 | 0.55 | 0.43 |

Example 17

*Chlorella variabilis* was grown with combination of 2%, 5%, 10% JOCH with 2% GL7 in tap water to grow the cells of *Chlorella variabilis* in static condition with light. Growth rate was measured spectrophotometrically (OD at 540 nm) up to 21 days. After 21 days; the cell mass was harvested by centrifugation at 11,000 rpm for 10 min at 30° C., and cell pellet was washed twice with distilled water and dried in oven (60° C.) for 16 hr. Lipid was extracted from weighed dried mass using Chloroform:Methanol (2:1), and after evaporation of solvent the total Lipid was obtained. In the 2% GL7 and 10% JOCH highest biomass 3.1 gram was obtained with of 22.58% (0.7 gram) lipid content.

TABLE 3

| Day | 2% GL-7 + 2% JOCH Example 17a | 2% GL-7 + 5% JOCH Example 17b | 2% GL-7 + 10% JOCH Example 17c |
|---|---|---|---|
| Dry biomass (gram) | 2.8 | 1.75 | 3.1 |
| Lipid (gram) | 0.2 | 0.34 | 0.7 |
| Yield % | 7.14 | 19.42 | 22.58 |

Example 18

*Chlorella variabilis* was grown in sea water with different concentration of GL7 & JOCH in 200 ml culture medium at static condition in light incubation. Growth rate was measured spectrophotometrically (OD at 540 nm) up to 2 days. In one set JOCH is added initially (0 day) & GL-7 is added after 10 days of growth and biomass & lipid composition change is observed. After 21 days; the cell mass was harvested by centrifugation at 11,000 rpm for 10 min at 30° C., and cell pellet was washed twice by distilled water and dried in oven for 16 hr. Lipid was extracted from weighed dried mass using Chloroform:Methanol (2:1), and after evaporation of solvent the total lipid was obtained. Biomass of Chlorella & lipid content was found maximum in media containing 1% JOCH (0 day) and GL7 is added at 10th day in sea water.

TABLE 4

| Parameter | 1% JOCH + GL-7 (After 10 Days) in sea water Example 18a | 1% JOCH + GL-7 (After 10 Days) in 1:2 diluted sea water Example 18b | 1% GL-7 + 1% JOCH in sea water Example 18c | 1% GL-7 + 1% JOCH in 1:2 diluted sea water Example 18d |
|---|---|---|---|---|
| Biomass (gm) | 0.62 gm | 0.47 gm | 0.51 gm | 0.25 gm |
| Lipid (gm) | 0.132 gm | 0.103 gm | 0.101 gm | 0.0401 gm |
| Yield (%) | 21.29 | 21.9 | 19.80 | 16.04 |

Example 19

Protection of Chlorella variabilis from UV-damage through the dye of 2,5-thiophenediylbis(5-tert-butyl-1,3-benzoxazole) class used in concentration of 0.33% was studied under lab conditions by exposing 50 ml of culture under UV-lamp (30 W) of Laminar air flow for 12 hours kept at a distance of 10 cm and 50 cm from the source of UV-light. The cell damage was quantitatively determined through UV-visible spectrophotometer (OD at 540nm) and UV-fluorescence studies (excitation at 540 nm); UV effect on dry cell mass and lipid content of Chlorella was studied that revealed the following results.

TABLE 5

| Culture | Dry weight of Chlorella biomass | lipid content | lipid |
|---|---|---|---|
| Chlorella (UV unexposed) | 62 | 16.4 | 26.45 |
| Chlorella + dye (UV unexposed) | 73.3 | 16.0 | 21.82 |
| Chlorella + dye (10 cm UV exposed) | 56.8 | 8.0 | 14.08 |
| Chlorella (10 cm UV exposed) | 51.5 | 5.1 | 9.9 |
| Chlorella + dye (50 cm UV exposed) | 74.7 | 15.4 | 20.6 |
| Chlorella (50 cm UV exposed) | 53.8 | 8.6 | 15.98 |

Example 20

Protection of Chlorella variabilis from UV-damage through the dye of 2,5-thiophenediylbis(5-tert-butyl-1,3-benzoxazole) class used in concentration of 0.33% was studied under outdoor cultivation on terrace during peak period of Indian summer conditions especially in Gujarat with following radiation data (table xy an) 100 ml of culture was exposed under the direct sunlight for two days. The total UV radiation was measured in wm-throughout the day using Eppley TUVR (as shown in Figure.) The cell damage was quantitatively determined through UV-visible spectrophotometer (OD at 540 nm) and UV-fluorescence studies (excitation at 540 nm).

TABLE 6

| Culture | Dry weight of Chlorella biomass (mg) | Lipid content (mg) | Lipid % |
|---|---|---|---|
| UV untreated Chlorella | 135.6 | 11.1 | 8.185 |
| UV untreated Chlorella with dye | 129.1 | 13.7 | 10.611 |
| Chlorella outdoor | 163 | 12.99 | 7.969 |
| Chlorella + dye outdoor | 140 | 17.4 | 12.428 |

Outdoor expriment depicting effect of UV radiations on Chlorella biomass and lipid.

Outdoor experiment depicting effect of UV radiations on Chlorella biomass and lipid.

Example 21

Chlorella variabilis was grown in sea water with different concentration of biodiesel byproduct (BWR 6 & JOCH) with 200 ml culture medium at static condition in light incubation. Growth rate was measured spectrophotometrically (OD at 540 nm) up to 18 days. JOCH is added initially (0 day) & BWR-6 is added after 10 days of growth and biomass & lipid composition change is observed. After 18 days; the cell mass was harvested by centrifugation at 11,000 rpm for 10 min at 30° C., and cell pellet was washed twice by distilled water and dried in oven for 16 hr. Lipid was extracted from weighed dried mass using Chloroform:Methanol (2:1), and after evaporation of solvent the total lipid was obtained.

TABLE 7

| Parameter | 1% JOCH + 2% BWR-6 (after 10 days) in sea water Example 21a | 1% JOCH + 2% BWR-6 (after 10 days) in 1:2 dil. sea water Example 21b | 1% JOCH + 5% BWR-6 (after 10 days) in sea water Example 21c | 1% JOCH + 5% BWR-6 (after 10 days) in 1:2 dil. sea water Example 21d |
|---|---|---|---|---|
| Biomass (gm) | 0.4410 gm | 0.4370 gm | 0.5580 gm | 0.4540 gm |
| Lipid (gm) | 0.0455 gm | 0.048 gm | 0.0785 gm | 0.1505 gm |
| Yield % | 10.31 | 10.98 | 14.06 | 33.14 |

Example 22

Chlorella variabilis was grown in sea water with different concentration of biodiesel byproduct (BWR 6 & JOCH) with 200 ml culture medium at static condition in light incubation. Growth rate was measured spectrophotometrically (OD at 540 nm) up to 10 days. JOCH is added initially (0 day) & BWR-6 is added after 4 days of growth and biomass & lipid composition change is observed. After 10 days; the cell mass was harvested by centrifugation at 11,000 rpm for 10 min at 30° C., and cell pellet was washed twice by distilled water and dried in oven for 16 hr. Lipid was extracted from weighed dried mass using Chloroform:Methanol (2:1), and after evaporation of solvent the total Lipid was obtained.

TABLE 8

| Parameter | 1% JOCH + 2% BWR-6 (After 4 Days) in sea water Example 22a | 1% JOCH + 2% BWR-6 (After 4 Days) in 1:2 diluted sea water Example 22b | 1% JOCH + 5% BWR-6 (After 4 Days) in sea water Example 22c | 1% JOCH + 5% BWR-6 (After 4 Days) in 1:2 diluted sea water Example 22d |
|---|---|---|---|---|
| Biomass (gm) | 0.3440 gm | 0.3020 gm | 0.3785 gm | 0.2635 gm |
| Lipid (gm) | 0.014 gm | 0.019 gm | 0.0524 gm | 0.0217 gm |
| Yield % | 4.2 | 6.29 | 13.8 | 8.26 |

Example 23

*Chlorella variabilis* was grown in diluted Zarrouk's medium (1:2 in tap water) in 100 liter culture medium in open plastic tank (l×b×h 1.47 m×0.74 m·0.22 m) with 10% inoculum of 0.6 OD at 540 nm. Growth rate was measured spectrophotometrically (OD at 540 nm) up to 16 days. After 16 days; the cell mass was settled by pH adjustment pH 4.5 using $H_3PO_4$ after which the dewatered cells were sundried. Lipid was extracted from dried biomass using Chloroform:Methanol (2:1), and after evaporation of solvent the total lipid was obtained. Biomass obtained was 401.21 gram in 100 liter, having lipid content of 97.29 gram i.e. 24.25% cell dry weight.

Example 24

*Chlorella variabilis* was grown in 2% BWR-3 in tap water in 100 liter culture medium in open plastic tank (l×b×h 1.47 m×0.74 m·0.22 m) with 10% inoculum of 0.6 OD at 540 nm. Growth rate was measured spectrophotometrically (OD at 540 nm) up to 16 days. After 16 days; the cell mass was settled by pH adjustment pH 4.5 using $H_3PO_4$ after which the dewatered cells were sundried. Lipid was extracted from dried biomass using Chloroform:Methanol (2:1), and after evaporation of solvent the total lipid was obtained. Biomass obtained was 380:12 gram in 100 liter, having lipid content of 90.53 gram i.e. 23.81% cell dry weight.

Example 25

*Chlorella variabilis* was grown in 2% BWR-3 in sea water: tap water (1:2) in 100 liter culture medium in open plastic tank (l×b×h 1.47 m×0.74 m·0.22 m) with 10% inoculum of 0.6 OD at 540 nm. Growth rate was measured spectrophotometrically (OD at 540 nm) up to 16 days. After 16 days; the cell mass was settled by pH adjustment pH 4.5 using $H_3PO_4$ after which the dewatered cells were sundried. Lipid was extracted from dried biomass using Chloroform:Methanol (2:1), and after evaporation of solvent the total lipid was obtained. Biomass obtained was 440.01 gram in 100 liter, having lipid content of 150.61 gram i.e. 34.23% cell dry weight.

TABLE 9

Percentage of fatty acid in algal oil

| Sr. No | Fatty acid | Percentage % |
| --- | --- | --- |
| 1 | Caprylic acid | 0.047 |
| 2 | Myristic acid | 0.413 |
| 3 | Pentadecanoic acid | 0.207 |
| 4 | Palmitoleic acid | 13.82 |
| 5 | Palmitic acid | 34.46 |
| 6 | Heptadecanoic acid | 1.38 |
| 7 | Oleic acid | 25.46 |
| 8 | Steric acid | 23.28 |
| 9 | 11-Eicosenoic acid | 0.67 |
| 10 | Behenic acid | 0.24 |

Advantages of the Invention

1. Utilization of co-streams of *Jatropha* methyl ester for Mixotrophic growth of Microalgae and conversion into lipids in an efficient and cost-effective manner.
2. Protection of the mass culture of *Chlorella variabilis* from UV-damages by adding a dye and maintaining the biomass productivity.
3. Improvement in the yield and overall lipid productivity by having fed batch system of growing Microalgal culture initially with JOCH in sea water+tap water (1:2) and after few days crude glycerol, both obtained as byproducts during the process of *Jatropha* biodiesel.

We claim:

1. An integrated process for the production of oil bearing *Chlorella variabilis* for lipid extraction utilizing by-products of *Jatropha* methyl ester (JME) production from whole seeds of *Jatropha* and the process comprising the steps of:
    i) providing deoiled cake as by-product of *Jatropha* methyl ester (JME) production having 4-6% (w/w) nitrogen of *Jatropha* seeds;
    ii) hydrolyzing the deoiled cake as provided in step (i) with hot acidic aqueous solution followed by adjusting pH in the range of 5.5 to 8.5 with alkaline materials to obtain a nitrogen-rich *Jatropha* oil cake hydrolysate (JOCH);
    iii) providing crude glycerol containing methanol-depleted glycerol layer containing by product of JME production obtained by washing crude fatty acid methyl ester obtained by transesterification of oil obtained from *Jatropha* with methanol and then distilling off residual methanol;
    iv) adding 1-5% (w/v) of crude glycerol containing methanol-depleted glycerol as provided in step (iii) to 1-10% (v/v) of *Jatropha* oil cake hydrolysate as obtained in step (ii) to prepare growth and production medium for *Chlorella variabilis*;
    v) inoculating 1-10% (v/v) of *Chlorella variabilis* culture into growth and production medium as obtained in step (iv) and incubating for a period in the range of 7 to 15 days at a pH in the range of 7.0-8.0 at a temperature in the range of 25-40° C. to obtain lipid containing biomass;
    vi) optionally inoculating 1-10% (v/v) of *Chlorella variabilis* culture into growth and production medium as obtained in step (iv) and adding UV-specific dye during outdoor biomass production to protect from UV damage at a temperature in the range of 40-50° C. to maintain the viability of the culture, and incubating for a period in the range of 7 to 15 days at a pH in the range of 7.0-8.0 at a temperature in the range of 25-40° C. to obtain lipid containing biomass;
    vii) drying the biomass as obtained in step (v to vi) in sun or directly using the wet biomass for lipid extraction;
    viii) extracting the lipid from biomass as obtained in step (vii).

2. An integrated process as claimed in claim 1, wherein the acid used is selected from the group consisting of $H_3PO_4$ and $H_2SO_4$.

3. An integrated process as claimed in claim 1, wherein the alkaline material is selected from the group consisting of crude glycerol layer containing by product of JME production obtained by washing crude fatty acid methyl ester obtained by transesterification of oil obtained from *Jatropha* with methanol and then distilling off residual methanol, potassium hydroxide and magnesium hydroxide.

4. An integrated process as claimed in claim 1, wherein the UV dye used is 2,5-thiophenediylbis(5-tert-butyl-1,3-benzoxazole).

5. An integrated process as claimed in claim 1, wherein yield of the lipid with respect to cell dry weight are in the range of 20 to 35%.

6. An integrated process for the production of oil bearing *Chlorella variabilis* for lipid extraction utilizing by-products of *Jatropha* methyl ester (JME) production from whole seeds of *Jatropha* and the process comprising the steps of:
    i) providing a crude glycerol-containing methanol-depleted glycerol layer-containing by product obtained by washing crude fatty acid methyl ester obtained by transesterification of oil obtained from *Jatropha* with methanol and then distilling off residual methanol;
    ii) inoculating 1-10% (v/v) of *Chlorella variabilis* culture on the $1^{st}$ day of growth with tap water, for initial 4 to 10 days incubation with only seawater or 1:2 diluted seawater in tap water and after $4^{th}$ to $10^{th}$ day subsequently adding methanol-depleted glycerol-containing by product as specified in step (i) to obtain lipid containing biomass;

iii) drying the biomass as obtained in step (ii) in sun or directly using the wet biomass for lipid extraction;

iv) extracting the lipid from biomass as obtained in step (iii).

\* \* \* \* \*